United States Patent [19]

Bradley

[11] Patent Number: 5,302,759
[45] Date of Patent: Apr. 12, 1994

[54] PROCESS FOR SEPARATING KETONES FROM ALCOHOLS

[75] Inventor: Christopher K. Bradley, Ashford, Great Britain

[73] Assignee: Unilever Patent Holdings B.V., Vlaardingen, Netherlands

[21] Appl. No.: 957,484

[22] Filed: Oct. 7, 1992

[30] Foreign Application Priority Data

Oct. 11, 1991 [EP] European Pat. Off. ........ 91309387.8

[51] Int. Cl.$^5$ ............................................ C07C 45/85
[52] U.S. Cl. .................................... 568/366; 568/410; 568/324
[58] Field of Search ........................ 568/410, 366, 324; 556/54

[56] References Cited

U.S. PATENT DOCUMENTS

| | | | |
|---|---|---|---|
| 2,457,257 | 12/1948 | Michael et al. | 568/410 |
| 2,555,553 | 6/1951 | Michael et al. | 560/410 |
| 2,708,205 | 5/1955 | Haslam | 556/54 |
| 2,719,863 | 10/1955 | Haslam | 556/54 |
| 2,920,089 | 1/1960 | Samour | 556/54 |
| 3,721,689 | 3/1973 | Bardinet | 556/54 |

*Primary Examiner*—James H. Reamer
*Attorney, Agent, or Firm*—Cushman, Darby & Cushman

[57] ABSTRACT

The invention relates to a process for separating ketones from alcohols by chemical interaction. More specifically, a difference in chemical reactivity between ketones and alcohols with a third compound is used as a basis for the separation. The third compound in this case is an organo-metallic compound of the general formula $M(X)_n$. Herein is M a polyvalent metal atom, n equals the valence of the metal and X is an organic or inorganic group or atom, with the proviso that at least one organic group is present in the organo-metallic compounds according to the invention. If the ketone-alcohol mixture is subjected to the organo-metallic compounds according to the invention under suitable conditions, an exchange reaction between the alcohols and the groups X takes place, and the ketones can be isolated from the reaction mixture in a conventional way.

7 Claims, No Drawings

PROCESS FOR SEPARATING KETONES FROM ALCOHOLS

The invention relates to a process for separating ketones from alcohols by chemical interaction. More particularly the invention relates to a process for a separation using an organo-metallic compound which preferentially reacts with alcohols rather than with ketones.

From US-A-3,839,473 it is known to remove alkane-diols from alkanols by contacting the mixture with polyvalent metal compounds such as: $M(OR_1)_x(R_2)_y$ and $M(OR_1)_x(OR_2)_y$ where M is aluminium, titanium, or boron, $R_1$ and $R_2$ are alkyl groups, $x+y$ is 3 or 4. The separation process is based on the preferential reaction of alkane-diols with the organo-metallic compounds.

JP 84 123 501, on the other hand, describes a process for drying organic solvents. The solvent to be dried is distilled in the presence of a hydrolyzable organo-metallic compound whereby the water is removed due to reaction with the metal compound. The process is exemplified by drying lower aliphatic alcohols, acetylacetone and ethylacetate.

In many processes ketones are obtained in admixture with alcohols. Usual procedures for separating alcohols from ketones such as distillation, are not always applicable or completely satisfactory because e.g. azeotrope formation occurs or the boiling points of the ketone and alcohol concerned are too close to obtain satisfactory separation.

Therefore, there is a need for a convenient process for separating ketones from alcohols in those cases where conventional procedures are impossible or undesirable or where a more complete separation is desired than can be obtained by conventional procedures.

It has now been found that certain organo-metallic compounds can be used for such a process due to a considerable preference in chemical reactivity of such compounds to alcohols compared to ketones. Said organo-metallic compounds are of the type $M(X)_n$, wherein is M a polyvalent metal atom, n is its valence and X denotes an organic or inorganic atom or group (e.g. a halogen atom), with the proviso that at least one organic group is present in the organo-metallic compounds according to the invention. Mixtures of various organo-metallic compounds having dissimilar metals and/or dissimilar atoms or groups X may also be used.

Organo-metallic compounds according to the invention react with a mixture of one or more ketones and one or more alcohols (under suitable conditions), leading to an exchange between an organic group X and the alcohol present, whereby one or more organic groups X per molecule $M(X)_n$ are liberated under formation of compound HX, while the alcohol originally present in the ketone-alcohol mixture becomes bound to the organo-metallic compound. Thereafter, the ketones can be separated from the newly formed organo-metallic compound.

In theory, if an organo-metal of the type $M(X)_n$ is used, n molecules of the alcohol originally present could be bound to the metal. However, in practice it is preferred to use an excess of the amount of organo-metallic compound theoretically needed. The exact amount to be used will depend on, inter alia, the organo-metallic compound used, the type and amount of ketone(s) and alcohol(s) present in the mixture and the desired degree of separation.

Preferred polyvalent metals for the said compounds are aluminium, titanium and boron. A most preferred metal is titanium.

Different organic groups may be present in the compounds according to the invention. Likewise, different inorganic atoms or groups may be present in the compounds according to the invention. This can be represented by e.g. $M(X_1)_p(X_2)_q$, wherein $p+q=n$. A compound like monochlorotriethoxytitanate is therefore included in the definition of the compounds according to the invention.

However, it is preferred that all radicals X are organic groups, and more preferred are alkyl and alkoxy groups for it. The alkyl groups will be denoted by "R" and the alkoxy groups will be denoted by "OR".

Even more preferred for the organic group are alkoxy groups having 1 to 10 carbon atoms, giving alkoxides of polyvalent metals. Still more preferred for the organic group are alkoxy groups comprising 1 to 5 carbon atoms. Most preferred are metal alkoxides according to the invention wherein OR is a methoxy-, ethoxy- or propoxy group, especially if the metal M in the compound $M(OR)_n$ is titanium, wherein n equals 4.

In the case the liberated X is an alkyl group (R), alkanes (HR) are formed due to the exchange reaction and likewise, if the liberated X is an alkoxy group (OR), alcohols (HOR) are formed. In the latter case the reaction is a transalcoholysis. If $M(X)_n$ comprises both alkyl and alkoxy groups, the above disclosed reactions may occur simultaneously or subsequently.

Preferably the metal alkoxide is chosen such that the alcohol liberated by the transalcoholysis reaction (in the case a metal alkoxide is used in the process) has a boiling point below the boiling points of the ketones and alcohols present in the mixture to be separated. Thus, the transalcoholysis can be forced to substantial completion by removing the liberated alcohol from the reaction mixture by e.g. distillation whereby the ketone and the newly obtained metal alkoxide remain in the reaction mixture, whereafter the ketone may be separated in any conventional way, e.g. by distillation.

The process according to the invention is very suitable for removing alcohols from a ketone/alcohol mixture wherein the ketone is carvone, especially if one or more of the alcohols is a terpene alcohol.

The following examples serve to illustrate the process according to the invention which is in no way limited thereto.

EXAMPLE 1

A mixture of carvone (27 g), α-terpineol (2 g, 13 mmol) and titanium n-propoxide (3.7 g, 13 mmol) was distilled through a 15x1.5 cm Vigreux column. After distilling off the isopropanol, the fraction collected at 100° C., 14 mbar (1.4 kPa) was carvone (25.9 g) substantially free of α-terpineol, representing a 96% recovery of the carvone.

EXAMPLE 2

A mixture of carvone (27 g), α-terpineol (2 g, 13 mmol) and titanium methoxide (75%)(2.2 g, 9.6 mmol) was distilled through a 15x1.5 cm Vigreux column. After distilling off the methanol, the fraction collected at 96° C., 11 mbar (1.1 kPa) was carvone (25.7 g) substantially free of α-terpineol, representing a 95% recovery of the carvone.

EXAMPLE 3

A sample of distilled crude carvone (containing carvone 95.5% w/w and α-terpineol 2% w/w) was treated with titanium ethoxide (50% in heptane), using 0.75 mol titanium ethoxide per mol of α-terpineol present. This solution was passed through a Leybold KDL-1 short-path molecular still (oil jacket temperature 115° C., pressure 40 mmHg (5.3 kPa)). The carvone is obtained in solution in heptane, whereas the liberated ethanol is collected in a cold trap. The heptane was removed from the carvone by using a rotary evaporator, after which 92.6 g carvone with less than 0.08% α-terpineol present was obtained, representing a 97% recovery.

EXAMPLE 4

A sample of distilled crude carvone (501 g) containing carvone 95.5% w/w and α-terpineol 2% w/w was treated with titanium ethoxide (50% in heptane), using 0.85 mol of titanium ethoxide per mol of α-terpineol present. This solution was distilled through a 1mx2.5 cm Knitmesh fractionating column under reduced pressure. Fractions collected at 90° C., 5.5 mbar (550 Pa) were 99.9+% pure and represented a 77% recovery of the carvone.

EXAMPLE 5

A mixture of 2-pentanone (40 g), 2-butanol (3.7 g, 50 mmol) and titanium ethoxide (11.4 g, 50 mmol) was distilled through an 18 cm Vigreux column at atmospheric pressure. The distillate collected from 96 to 101° C. (37 g), was free from 2-butanol and contained 0.5 g of ethanol.

I claim:

1. A process for separating ketones from alcohols comprising the steps of:
    reacting a mixture of ketones and alcohols with an organometallic compound $M(X)_n$ to form compound(s) HX, wherein M is chosen from aluminum, titanium and boron, n is the valence of M and X denotes equal or different organic groups chosen from alkyl groups and alkoxy groups having up to 10 carbon atoms;
    liberating the newly formed compound(s) HX from the reaction mixture by distillation;
    separating the ketones from the organometallic compound formed by a reaction between $M(X)_n$ and the alcohols in the mixture.

2. A process according to claim 1, wherein $M(X)_n$ is a metal alkoxide $M(OR)_n$ and R denotes aliphatic alkyl groups having 1 to 10 carbon atoms.

3. A process according to claim 2, wherein in the polyvalent metal alkoxide $M(OR)_n$ R denotes aliphatic aklyl groups having 1 to 5 carbon atoms.

4. A process according to claim 3, wherein $M(OR)_n$ is one of titanium methoxide, titanium ethoxide, titanium n-propoxide, titanium iso-propoxide or a combination thereof.

5. A process according to claim 4, wherein HX is separated by distillation.

6. A process according to claim 1, wherein the ketone is carvone.

7. A process according to claim 1, wherein the alcohol originally present in the ketone-alcohol mixture is a terpene alcohol.

* * * * *